(12) United States Patent
Weiland

(10) Patent No.: US 9,023,109 B2
(45) Date of Patent: *May 5, 2015

(54) IMPLANT FOR TRANSFORAMINAL INTRACORPOREAL FUSION

(71) Applicant: Advanced Medical Technologies AG, Nonnweiler-Braunshausen (DE)

(72) Inventor: Peter Weiland, Nonnweiler-Braunhausen (DE)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,370

(22) Filed: Aug. 5, 2013

(65) Prior Publication Data

US 2014/0039627 A1 Feb. 6, 2014

Related U.S. Application Data

(63) Continuation of application No. 12/308,148, filed as application No. PCT/EP2005/000881 on Jan. 28, 2005, now Pat. No. 8,506,629.

(51) Int. Cl.
*A61F 2/44* (2006.01)
*A61F 2/46* (2006.01)
(Continued)

(52) U.S. Cl.
CPC ............. *A61F 2/4455* (2013.01); *A61F 2/4465* (2013.01); *A61F 2/4611* (2013.01); *A61F 2002/2835* (2013.01); *A61F 2002/3008* (2013.01); *A61F 2002/30133* (2013.01); *A61F 2002/30471* (2013.01); *A61F 2002/3054* (2013.01); *A61F 2002/30601* (2013.01); *A61F 2002/30772* (2013.01); *A61F 2002/30878* (2013.01); *A61F 2002/4475* (2013.01); *A61F 2002/4627* (2013.01); *A61F 2002/4629* (2013.01); *A61F 2220/0091* (2013.01);
(Continued)

(58) Field of Classification Search
USPC ........................................................ 623/17.16
See application file for complete search history.

(56) References Cited

U.S. PATENT DOCUMENTS

| 5,571,190 A | 11/1996 | Ulrich et al. |
| 5,571,192 A | 11/1996 | Schonhoffer |
| 5,989,290 A | 11/1999 | Biedermann et al. |

(Continued)

FOREIGN PATENT DOCUMENTS

| CA | 2216450 A1 | 3/1998 |
| DE | 4328062 A1 | 2/1995 |

(Continued)

*Primary Examiner* — Thomas J Sweet
*Assistant Examiner* — Brian Dukert

(57) ABSTRACT

The invention relates to an implant for the transforaminal intracorporeal fusion of lumbar vertebral column segments. At least some sections of the surface areas that are in direct contact with the spinal column are provided with an anti-dislocation mechanism (1) while an attachment part (4) for a positioning instrument (10) is provided in or on the implant and holes (6) or hollow spaces are disposed in the implant for filling purposes. According to one embodiment of the invention, the attachment part is configured as a revolute joint. In a further embodiment, the implant member has the shape of a sickle, the curvature of which is oriented ventrally and the interior of which is oriented dorsally. The attachment part is located at one end of the sickle while the opposite end of the sickle has a beak-type, tapering shape (5). At least one filling hole is provided between the sickle walls.

19 Claims, 2 Drawing Sheets

(51) Int. Cl.
*A61F 2/28* (2006.01)
*A61F 2/30* (2006.01)

(52) U.S. Cl.
CPC . *A61F2230/0015* (2013.01); *A61F 2250/0098* (2013.01)

(56) References Cited

U.S. PATENT DOCUMENTS

| | | | | |
|---|---|---|---|---|
| 6,395,031 | B1* | 5/2002 | Foley et al. | 623/17.11 |
| 2003/0139813 | A1* | 7/2003 | Messerli et al. | 623/17.11 |
| 2004/0153065 | A1 | 8/2004 | Lim | |
| 2005/0027360 | A1* | 2/2005 | Webb et al. | 623/17.11 |
| 2005/0096745 | A1 | 5/2005 | Andre et al. | |
| 2005/0131536 | A1* | 6/2005 | Eisermann et al. | 623/17.11 |

FOREIGN PATENT DOCUMENTS

| | | |
|---|---|---|
| DE | 4423257 A1 | 1/1996 |
| DE | 19509317 A1 | 9/1996 |
| DE | 19519101 A1 | 11/1996 |
| DE | 29616778 U1 | 1/1998 |
| EP | 1290985 A2 | 3/2003 |
| FR | 2841125 A1 | 12/2003 |
| WO | 0195838 A1 | 12/2001 |
| WO | 0217823 A1 | 3/2002 |
| WO | 2005041825 A1 | 5/2005 |

* cited by examiner

IMPLANT FOR TRANSFORAMINAL INTRACORPOREAL FUSION

This application is a continuation application of co-pending U.S. patent application Ser. No. 12/308,148 filed Jul. 6, 2009, which claims the benefit of International Application No. PCT/EP2005/000881 filed Jan. 28, 2005. The entire disclosure of these documents is herein incorporated by reference into the present application.

BACKGROUND

The invention relates to an implant for the transforaminal interbody fusion of lumbar vertebral column segments, wherein at least some sections of the surface areas coming into direct contact with the vertebral column are provided with a dislocation protection, wherein further an engagement part for a positioning instrument is provided in or on the implant, and holes or hollow spaces are disposed in the implant for filling purposes.

Attempts are made to use minimal invasive surgery for spine operations. To this end, so-called PLIF (posterior lateral interbody fusion) operation techniques were developed. According to such an operation technique the intervertebral disc is removed through a posterior access, and the intervertebral space is filled with autologous bone. This technique is based on Cloward, who was the first to carry through such an operation in 1943. Further developments of the PLIF technique resulted in the application of a transforaminal access. This technique provides for the dorsal, transforaminal introduction of titanium cups—so-called cages—which are filled with autologous cancellous bone. At the same time, a dorsal instrumentation and stabilization is applied. The advantage of the briefly outlined method is that no transabdominal or retroperitoneal additional access has to be used.

The "Biotit Cage" of the company Ulrich serves to replace an intervertebral disc of the lumbar vertebral column. The cage is inserted through a dorsal access, with the application being possible in pairs or individually. This prior cage is substantially U-shaped and comprises a dislocation protection in the form of a striated structure. The implant material of the aforementioned cage is titanium or a titanium alloy, respectively, so that relatively large radiological windows are necessary to control the fusion.

Further known is a cage distributed by the company Stryker Orthopaedic, U.S.A., which is a cubic implant and can be implanted in pairs into the intervertebral space by an anterior as well as a posterior approach.

As regards the prior art, reference is additionally made to DE 43 28 062 A1, which relates to an implant for the replacement of vertebral bodies and/or the stabilization and fixation of the vertebral column. This implant consists of an implant body which is pushed onto a support rod transversely to the axis of the rod. The implant body according to DE 43 28 062 A1 is provided with a surface structure bearing against the vertebral bodies adjacent to the implant, so as to achieve a mutual fixation of the adjacent surfaces of the implant body on the one hand and the vertebral body on the other hand.

The prior art likewise includes height-adjustable vertebral body implants for the replacement of one or more vertebral bodies, e.g. according to DE 44 23 257 A1, DE 195 19 101 A1 or DE 195 09 317 A1. However, the production of these height-adjustable implants is very expensive, and their handling is complicated.

In the German utility model DE 296 16 778 U1 a vertebral body replacement is disclosed, which is inserted, for example, after a vertebral body resection to replace the missing vertebral body. Such replacements are made of a body-compatible material, with the front ends forming an irregular edge and the wall of the replacement having holes to provide for enough space to receive bone substance.

To insert the replacement according to DE 296 16 778 U1, a tool having a relatively long shank is used, with the shank having a threaded journal on the free end thereof to be brought into engagement with a threaded hole of the sleeve-shaped body so as to insert the same into the space of the resected vertebral body, in the predefined position between two adjacent vertebral bodies.

SUMMARY

Based on the foregoing it is the object of the invention to provide a further developed implant for the transforaminal interbody fusion of lumbar vertebral column segments. The implant is to have a high primary stability and allows a simple operative procedure in use.

In one embodiment, there is an implant for the transforaminal interbody fusion of lumbar vertebral column segments wherein at least some sections of the surface areas coming into direct contact with the vertebral column are provided with a dislocation protection, wherein further an engagement part for a positioning instrument is provided in or on the implant, and holes or hollow spaces are disposed in the implant for filling purposes, and wherein the engagement part is formed as a pivot joint or hinge joint. In one embodiment, there is a specific positioning instrument, wherein the insertion opening in the bolt has an inner thread.

Proceeding from an implant of which at least some sections of the surface areas coming into direct contact with the vertebral column are provided with a dislocation protection and which is provided with an engagement part for a positioning instrument, the further developed implant body has the shape of a sickle, with the convexity of the sickle being oriented ventrally and the inner side of the sickle being oriented dorsally.

The specific engagement part, which acts like a pivot joint, is located on one end of the sickle, while the opposite end of the sickle has a beak-like, tapering shape which serves as an insertion aid. At least one filling hole for receiving a large amount of bone substance is provided between the sickle walls of the implant body.

In one embodiment of the invention the engagement part is formed as a rotatable or pivotable bolt received in a through bore, the bolt having an insertion opening for an instrument which extends perpendicular to the longitudinal axis.

The sickle end with the engagement part is provided with a recess serving as access to the bolt and to the insertion opening for the aforementioned positioning instrument.

Preferably, the implant is made of a bioelastic synthetic material, specifically polyetheretherketone (PEEK). However, other appropriate implant materials are usable as well.

X-ray markers are incorporated in the bioelastic synthetic material. In the ventral, medial part these X-ray markers may be oriented vertically, while the orientation may be a horizontal, sagittal one at the implant tip.

Moreover, it is possible according to the invention to construct the bolt as a rotary part made of an X-ray detectable material.

Preferably, the structures of the dislocation protection have the shape of a truncated pyramid or truncated cone, or are realized in the form of spherical, cut bodies.

In a preferred embodiment of the invention the insertion opening of the bolt has an inner thread.

The positioning instrument used for handling the above-described implant is comprised of a shank and a sleeve, wherein the sleeve receives a pin with a threaded end and the threaded end is designed complementarily with respect to the inner thread of the insertion opening in the bolt.

Moreover, the pin with the threaded end can be moved by a rotary motion to be longitudinally displaceable relative to the sleeve. At the leading end of the sleeve a stopping face for the implant is provided, so that the implant held by the pin is fixable in the respective angular position by means of the bolt and the stopping face through tensioning.

In a surprising manner it has shown that the use of the bioelastic synthetic material PEEK provides for ideal conditions for a permanent fusion. The elastic properties similar to those of the bone prevent the implant from sinking in and support the fusion tendency. At the same time, the X-ray transparency ensures optimum postoperative diagnostics, namely without requiring, as compared to the prior art, larger radiological windows in the implant material.

Suitable, also relatively small and correspondingly positioned X-ray markers made, for example, of titanium or a titanium alloy material, allow the localization of the implant at any time.

With respect to the application and use of the implant, reference is made to the statements set forth below.

At first, the intervertebral disc space is emptied through a transforaminal access. To this end, appropriate grasping forceps or shaped curettes known per se are used.

After the discectomy, the intervertebral disc space is distracted by means of special distracters to the desired height. A suitable distraction height is reached as soon as the distractor is under tension and a respectively stable feeling is achieved. After the distraction, the required implant size, specifically the height of the implant is verified by means of special test implants. The positioning instrument according to the invention may already be used to hold these test implants.

Prior to the implantation of the implant, the size of which has then been ascertained, an appropriate material, e.g. cancellous bone, is preferably filled into the intervertebral disc space ventrally and into the opposite lateral side of the implant. The portion dorsally of the implant is filled as well.

For the implant, which is to be filled as well, a filling aid is used, into which the implant is inserted. The filling aid adopts the outer contour of the implant and defines a support frame.

After a suitable angle between the instrument and the implant was found by means of the positioning instrument and the stopping possibility, and after this angle was subjected to a corresponding fixation, the implant is inserted into the intervertebral disc space. Due to the implantation curve it is recommendable to adapt during the actual implantation the angle by a brief loosening motion, by making use of the advantageous effects of the positioning instrument.

A final positioning may be achieved by means of suited straight or bent push-pins. To obtain a correct implantation, the convex side of the implant is oriented ventrally and the two implant ends are oriented dorsally. To obtain all desired advantageous effects, the implant should be positioned as ventrally as possible.

After the implantation, the rest of the intervertebral disc space is filled, so as to ensure a reliable fusion.

The principle of the implant according to the invention is based on the tension of the annulus and the longitudinal ligaments in combination with a sufficient bone quality. In certain cases, an additional stabilization should be obtained by means of a dorsal fixator.

As was mentioned before, the implant may be made of a synthetic material, specifically of PEEK. This material is transparent to X-rays, and its mechanical properties are very similar to those of the body. To facilitate postoperative diagnostics, X-ray markers may be incorporated into the implant. A marker is located, for example, in the ventral, medial portion of the implant in vertical orientation, and another marker at the tip of the implant in horizontal, sagittal orientation. Additionally, the rotary part for receiving the instrument may act as an X-ray marker.

The invention shall be explained in more detail below by means of an embodiment and with the aid of figures.

DETAILED DESCRIPTION

Figure 1:
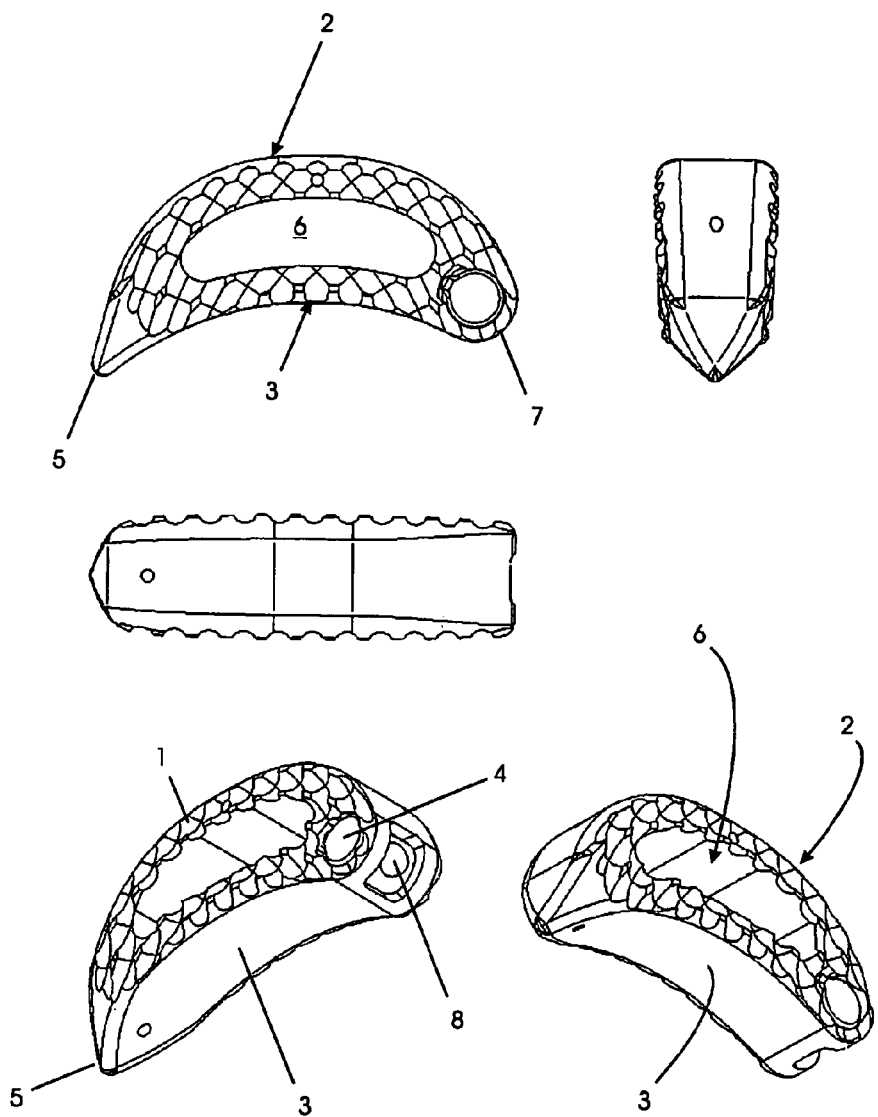
FIG. 1 shows various representations of the sickle-shaped implant according to the invention.

The surface areas of the implant for the transforaminal interbody fusion of lumbar vertebral column segments according to the embodiment, which come into direct contact with the vertebral column, have specific structures 1 serving as a dislocation protection. These structures 1 can have, for example, the shape of truncated pyramids or truncated cones, or may be realized in the form of cut, spherical bodies.

The implant body itself is sickle-shaped, whereby, in case of use, the convexity of the sickle 2 is oriented ventrally and the inner side of the sickle 3 is oriented dorsally.

An engagement part 4 is provided on one end of the sickle, and the other end of the sickle opposite to this engagement part has a tapering, beak-like shape 5.

At least one filling hole 6 is provided between the sickle walls.

The engagement part 4 is formed as a piovtable or rotatable bolt, which is located in a corresponding recess 7 in the implant.

The bolt comprises an insertion opening 8 with an inner thread (not shown), which extends substantially perpendicular to the longitudinal axis of the bolt.

Figure 2:
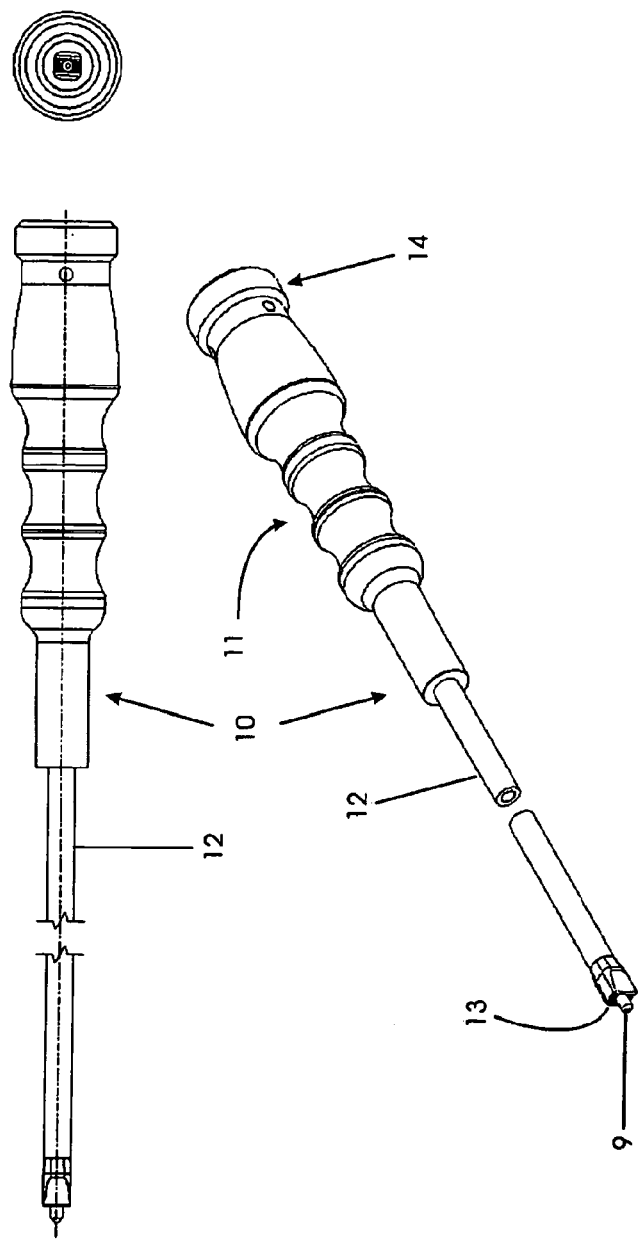
FIG. 2 shows a lateral view and a perspective representation of the implant positioning instrument.

The insertion opening 8 serves to receive a respective end 9 of the positioning instrument 10 (FIG. 2).

In the implant body, which is preferably made of a synthetic material, various X-ray markers may be incorporated, which are not illustrated in the figures, so that a postoperative localization of the implant can be achieved at any time.

According to FIG. 2 the positioning instrument 10 is comprised of a handle 11 with a sleeve 12.

A pin with a threaded end (part 9) is guided in the sleeve 12, wherein the threaded end is designed complementarily with respect to the inner thread of the insertion opening 8 in the bolt.

By a rotary motion on the cap 14 the pin 9 with the threaded end can be moved.

At the leading end of the sleeve 12 a stopping face 13 for the implant is provided, so that the implant held by the pin 9 is fixable in the respective angular position by means of the bolt and the stopping face 13.

The invention claimed is:
1. An implant for the transforaminal interbody fusion of lumbar vertebral column segments, comprising:
a main body including a top surface configured for disposal adjacent a first vertebral surface and a bottom surface situated opposite the top surface configured for disposal adjacent a second vertebral surface, the main body further including an inner side wall and an outer side wall situated opposite the inner side wall, and a first end portion and a second end portion situated opposite the first end portion, the second end portion having a throughbore formed therein and oriented transversely in the main body in a direction between the top surface and the bottom surface, and the main body having at least one filling hole adjacent to and separate from the throughbore; and an engagement part including a bolt being rotatably or pivotally received by the transversely-oriented throughbore, the bolt having a longitudinal axis extending between the top surface and the bottom surface, the bolt including a side wall and an insertion opening formed in the sidewall extending perpendicularly to the longitudinal axis.

2. An implant according to claim 1, wherein the top and bottom surfaces include dislocation protection elements.

3. An implant according to claim 2, wherein the dislocation protection elements have the shape of at least one of a truncated pyramid and a truncated cone.

4. An implant according to claim 1, wherein the main body has a sickle shape.

5. An implant according to claim 1, wherein the insertion opening in the bolt has an inner thread.

6. An implant according to claim 1, wherein the second end portion of the main body has an access recess formed therein, the access recess is in communication with the insertion opening formed in the bolt to allow a portion of a positioning instrument for positioning the implant between vertebrae to pass therethrough and into the insertion opening of the bolt.

7. An implant according to claim 1, wherein the second end portion of the main body has an access recess formed therein.

8. An implant according to claim 1, wherein the first end portion has a beak-like tapering shape.

9. An implant according to claim 1, wherein the implant is made of a bioelastic synthetic material.

10. An implant according to claim 9, wherein the bioelastic synthetic material comprises polyetheretherketone (PEEK).

11. An implant according to claim 1, wherein the implant is provided with X-ray markers.

12. An implant according to claim 1, wherein the bolt is a rotary part made of an X-ray detectable material.

13. An implant for the transforaminal interbody fusion of lumbar vertebral column segments, comprising:

a main body including a top surface having dislocation protection elements configured for engagement with a first vertebra and a bottom surface situated opposite the top surface having dislocation protection elements configured for engagement with a second vertebra, the main body further including an inner side wall and an outer side wall situated opposite the inner side wall, and a first end portion and a second end portion situated opposite the first end portion, the second end portion having a throughbore formed therein and oriented transversely in the main body in a direction between the top surface and the bottom surface, and the main body having at least one filling hole adjacent to and separate from the throughbore; and an engagement part including a bolt being rotatably disposed in the transversely-oriented throughbore, the bolt having a longitudinal axis extending between the top surface and the bottom surface, the bolt having a side wall and an insertion opening formed therein extending perpendicularly to the longitudinal axis of the bolt, the second end portion of the main body having an access recess formed therein, the access recess being in communication with the insertion opening formed in the bolt to allow a portion of a positioning instrument for positioning the implant between vertebrae to pass therethrough and into the insertion opening of the bolt.

14. An implant according to claim 13, wherein the main body has a sickle shape.

15. An implant according to claim 13, wherein the insertion opening in the bolt has an inner thread.

16. An implant according to claim 13, wherein the implant is made of a bioelastic synthetic material.

17. An implant according to claim 16, wherein the bioelastic synthetic material comprises polyetheretherketone (PEEK).

18. An implant according to claim 13, wherein the first end portion has a beak-like tapering shape.

19. An implant for the transforaminal interbody fusion of lumbar vertebral column segments, comprising:

a main body including a top surface having dislocation protection elements configured for engagement with a first vertebra and a bottom surface situated opposite the top surface having dislocation protection elements configured for engagement with a second vertebra, the main body further including an inner side wall and an outer side wall situated opposite the inner side wall, and a first end portion and a second end portion situated opposite the first end portion and defining an axis therebetween, the second end portion having a throughbore formed therein and oriented transversely to a first axis between the top surface and the bottom surface and the main body having at least one filling hole adjacent to and separate from the throughbore; and an engagement part including a bolt being rotatably disposed in the transversely-oriented throughbore, the bolt defining a longitudinal axis oriented transversely to the first axis and extending between the top surface and the bottom surface, the bolt having a side wall and an insertion opening formed therein extending perpendicularly to the longitudinal axis, the second end portion of the main body having an access recess formed therein, the access recess being in communication with the insertion opening formed in the bolt to allow a portion of a positioning instrument for positioning the implant between vertebrae to pass therethrough and into the insertion opening of the bolt.

\* \* \* \* \*